United States Patent
Lewis et al.

(10) Patent No.: US 8,765,982 B2
(45) Date of Patent: Jul. 1, 2014

(54) SYNERGISTIC ANTICOAGULANT COMPOSITION

(75) Inventors: David E. Lewis, Eau Claire, WI (US); Michael D. Caldwell, Milladore, WI (US)

(73) Assignee: Marshfield Clinic Health System, Inc., Marshfield, WI (US)

( * ) Notice: Subject to any disclaimer, the term of this patent is extended or adjusted under 35 U.S.C. 154(b) by 292 days.

(21) Appl. No.: 12/895,103

(22) Filed: Sep. 30, 2010

(65) Prior Publication Data

US 2011/0082194 A1    Apr. 7, 2011

Related U.S. Application Data

(60) Provisional application No. 61/247,724, filed on Oct. 1, 2009.

(51) Int. Cl.
   *C07D 303/17*     (2006.01)
   *C07D 303/14*     (2006.01)
   *A61K 31/336*     (2006.01)

(52) U.S. Cl.
   CPC ............ *C07D 303/17* (2013.01); *C07D 303/14* (2013.01); *A61K 31/336* (2013.01)
   USPC ........... 549/562; 549/554; 548/966; 548/968; 514/475; 514/511; 560/139

(58) Field of Classification Search
   CPC ... C07D 303/17; C07D 303/14; A61K 31/336
   USPC ........... 549/562, 554; 548/966, 968; 514/475, 514/511; 560/139
   See application file for complete search history.

(56) References Cited

U.S. PATENT DOCUMENTS 2,584,140 A * 2/1952 Lidov et al. .................. 568/732

OTHER PUBLICATIONS

Joshi, BS "The Synthesis of Radermachol." Journal of Organic Chemistry, 1994 59(26), 8220-32.*
Xi "New methods for the preparation of multiply substituted cyclopentadienes and related compounds" Topics in Catalysis vol. 35, No. 1-2, Jun. 2005.*
Marchand "Synthesis and Acid- and Base-promoted Ring Opening of Polycarbocyclic Oxiranes" Tetrahedron 54 (1998) 4459-4470.*

* cited by examiner

*Primary Examiner* — David K O Dell
(74) *Attorney, Agent, or Firm* — Tarolli, Sundheim, Covell & Tummino LLP

(57) ABSTRACT

A composition is provided that, when utilized in combination with warfarin, greatly improves the anticoagulant effects of warfarin in mammalian subjects. The composition is a compound having a naphthohydroquinone ring system substantially similar to the ring system of the reduced form of vitamin $K_1$ and has the general formula:

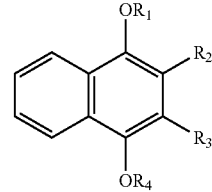

where $R_1$ and $R_4$ are hydrogen or acyl, $R_2$ is a saturated or unsaturated alkyl group with up to 6 carbons, and $R_3$ is a saturated or unsaturated alkyl group with up to 20 carbons, or $R_2$ and $R_3$ are part of a cyclic or polycyclic ring system.

3 Claims, 2 Drawing Sheets

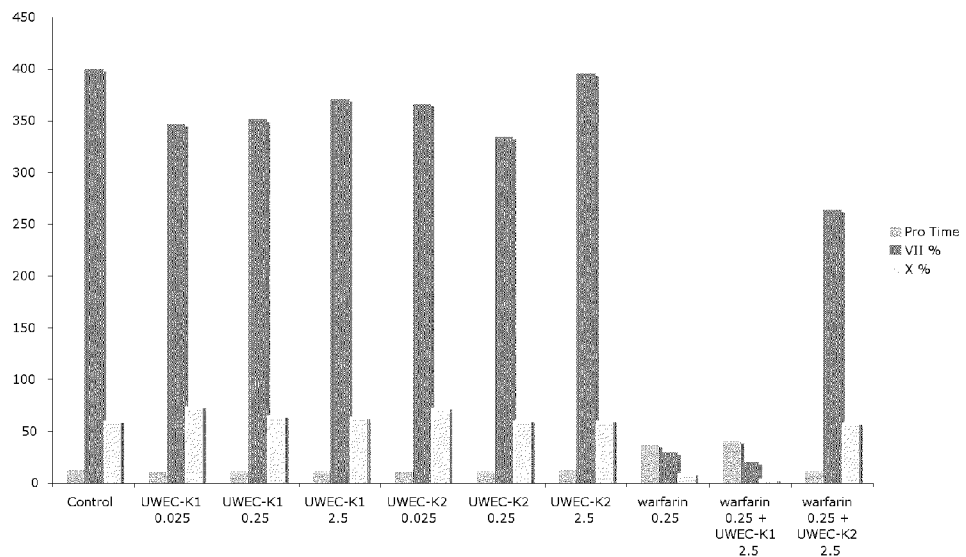
Figure 1. Effects of UWEC-K1 and UWEC-K2 on blood clotting in the presence and absence of warfarin after 4 days of separate administration and co-administration.
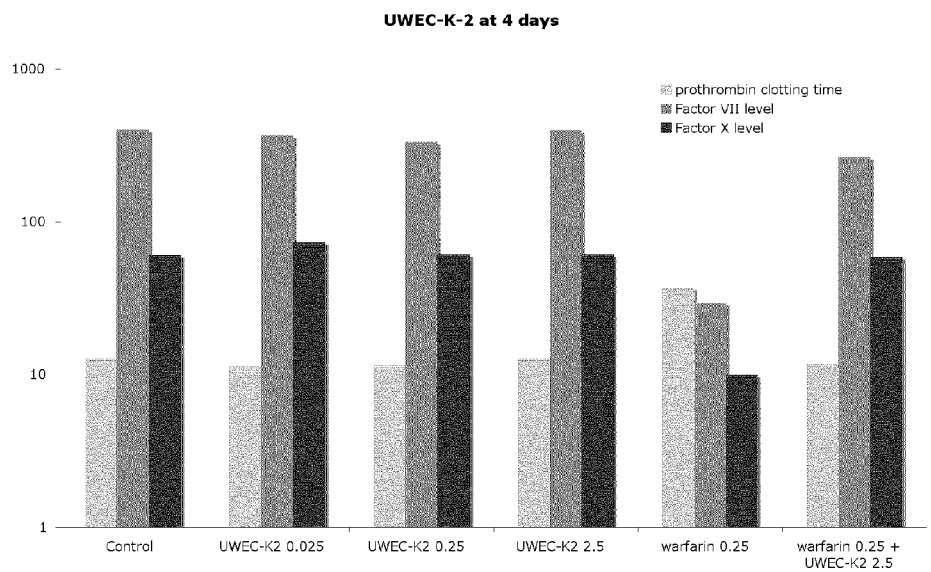
Figure 2. Effects of UWEC-K2 on blood clotting in the presence and absence of warfarin after 4 days of separate administration and co-administration.

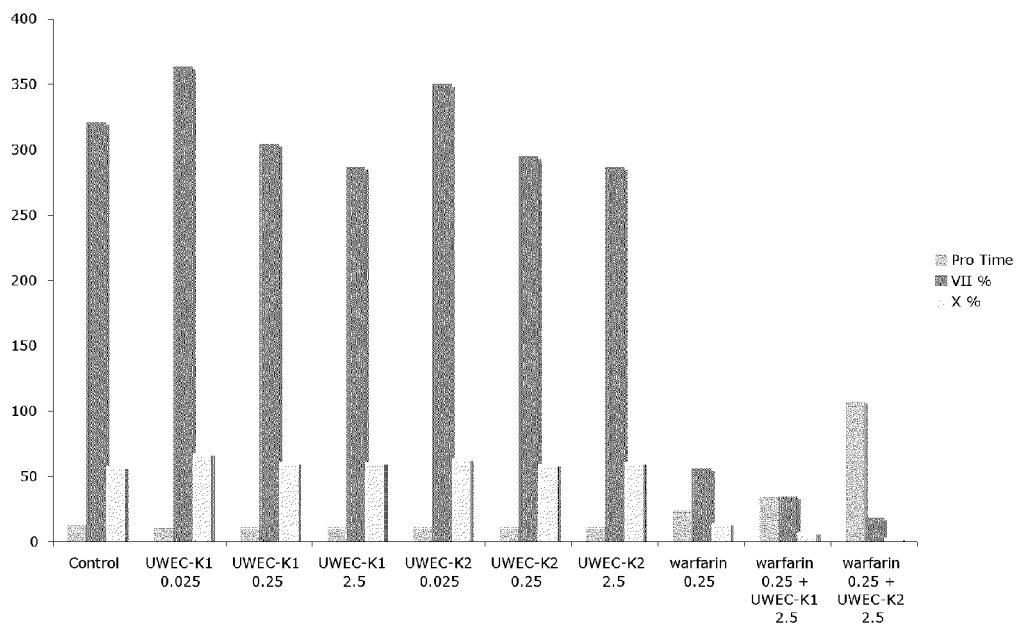
Figure 3. Effects of UWEC-K1 and UWEC-K2 on blood clotting in the presence and absence of warfarin after 10 days of separate administration and co-administration.
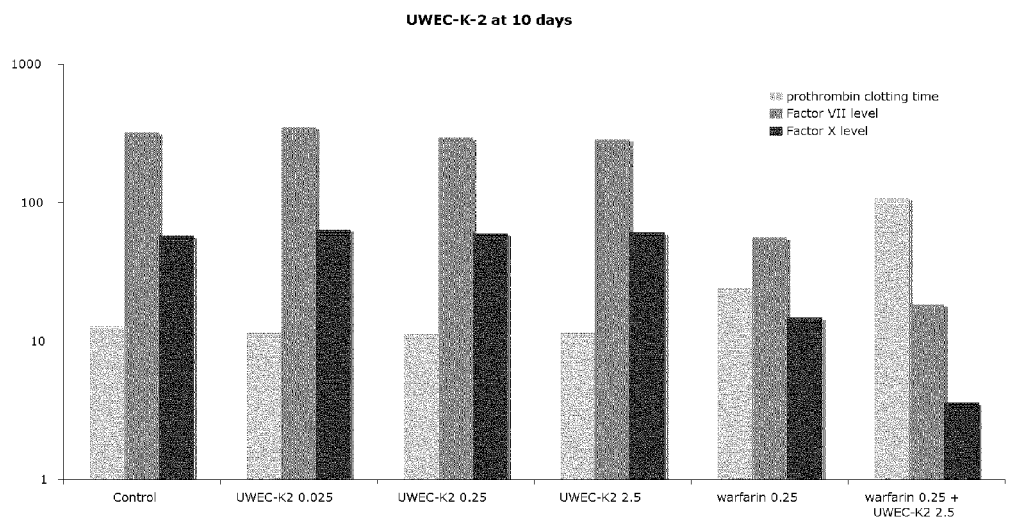
Figure 4. Effects of UWEC-K2 on blood clotting in the presence and absence of warfarin after 10 days of separate administration and co-administration.

SYNERGISTIC ANTICOAGULANT COMPOSITION

CROSS-REFERENCE TO RELATED APPLICATIONS

This application claims priority from U.S. Provisional Application Ser. No. 61/247,724, filed on Oct. 1, 2009, the entirety of which is hereby expressly incorporated by reference herein.

STATEMENT REGARDING FEDERALLY SPONSORED RESEARCH OR DEVELOPMENT

N/A

FIELD OF THE INVENTION

A new class of compounds has been developed that exhibit cooperative activity with warfarin to quadruple the anticoagulant activity of the coumarin, while not exhibiting significant anticoagulant activity when administered alone.

BACKGROUND OF THE INVENTION

Various anticoagulant compositions, and in particular, warfarin, have long been utilized in different human and animal modalities, e.g., in rodent poison. However, as a result of the continued use of the compound warfarin as a rat poison, rodents have become less susceptible to the effects of warfarin.

Therefore it is desirable to develop a composition that can be utilized either as a substitute or as a complement to existing anticoagulant compositions, such as warfarin, to increase the effectiveness of the anticoagulant.

SUMMARY OF THE INVENTION

According to one aspect of the present invention, a composition has been developed that, when utilized in combination with warfarin, acts to greatly improve the anticoagulant effects of warfarin in mammalian subjects. The composition is a compound having a naphthohydroquinone ring system substantially similar to the ring system of the reduced form of vitamin $K_1$ and has the general formula:

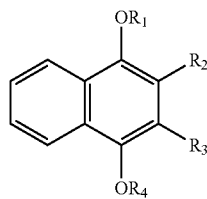

where $R_1$ and $R_4$ are hydrogen or acyl;

$R_2$ is a saturated or unsaturated alkyl group with up to 6 carbons; and $R_3$ is a saturated or unsaturated alkyl group with up to 20 carbons; or $R_2$ and $R_3$ are part of a cyclic or polycyclic ring system; and one or more hydrogen atoms of substituents $R_2$ and $R_3$ are replaced by a leaving group, in which the leaving group is chosen from an epoxide, an aziridine or N-acyl- or N-sulfonylaziridine, a halide (bromide, chloride or iodide), a sulfonate ester (methanesulfonate, benzenesulfonate, p-toluenesulfonate, p-bromobenzenesulfonate, p-nitrobenzenesulfonate, naphthalene-1-sulfonate, naphthalene-2-sulfonate);

and in which the leaving group is located so that it is not more than four atoms removed from the closest carbon atom of the naphthalene ring;

and which is capable of being oxidized in the presence or absence of an enzyme such as the vitamin K-dependent gamma-glutamyl carboxylase to give a structural analogue of vitamin K 2,3-epoxide that is capable of binding to the enzyme VKORC-1 in the vitamin K 2,3-epoxide binding site in the presence of warfarin.

Numerous additional aspects, features and advantages of the present invention will be made apparent from the following drawing figures taken together with the detailed description.

BRIEF DESCRIPTION OF THE DRAWING FIGURES

The drawings illustrate the best mode currently contemplated of practicing the present invention.

In the drawings:

FIG. 1 is a graph of the effects of UWEC-K1 and UWEC-K2 on blood clotting in the presence and absence of warfarin after 4 days of separate administration and co-administration;

FIG. 2 is a graph of the effects of UWEC-K2 on blood clotting in the presence and absence of warfarin after 4 days of separate administration and co-administration;

FIG. 3 is a graph of the effects of UWEC-K1 and UWEC-K2 on blood clotting in the presence and absence of warfarin after 10 days of separate administration and co-administration; and FIG. 4 is a graph of the effects of UWEC-K2 on blood clotting in the presence and absence of warfarin after 10 days of separate administration and co-administration.

DETAILED DESCRIPTION OF THE INVENTION

The compounds that have been developed are methanoanthracenediol derivatives, and they appear to act initially as sufficiently functional analogues of vitamin K to generate an analogue of vitamin K epoxide, and this then acts as a potentiator of the anticoagulant activity of warfarin in rats.

The compounds are prepared from the Diels-Alder adduct of 1,4-naphthoquinone and cyclopentadiene by aromatization of the dione ring by boiling with acetic anhydride and acetic acid in the presence of p-toluenesulfonic acid as the catalyst. The diacetate thus obtained is the first new compound, which we have designated UWEC-K1. This diacetate was epoxidized under standard conditions using m-chloroperoxybenzoic acid in dichloromethane to give the corresponding epoxide, which we have designated UWEC-K2.

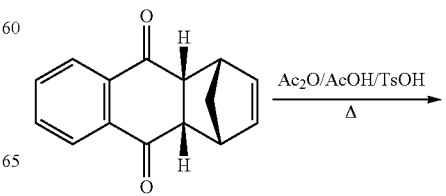

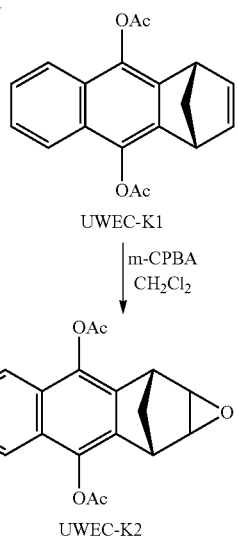

UWEC-K1

| m-CPBA
| CH₂Cl₂

UWEC-K2

These compounds were administered to rats in feed (p.o.) with and without warfarin. It was expected that the ester groups would be rapidly hydrolyzed by stomach acid or esterases in the gut of the rats to give analogues of dihydrovitamin K, which we designate UWEC-KH1 and UWEC-KH2 (corresponding to the compounds obtained by esterase- or stomach acid-catalyzed hydrolysis of UWEC-K1 and UWEC-K2, respectively).

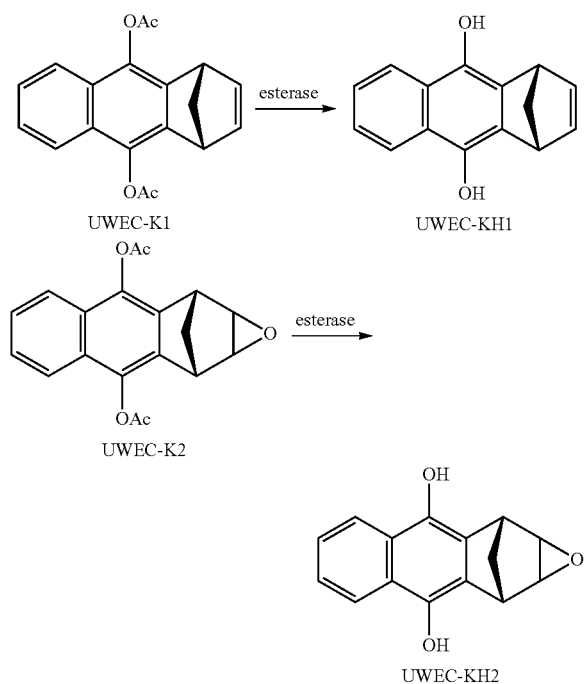

These compounds may be substrates for the vitamin K-dependent gamma-glutamyl carboxylase (GGCX), or may be subject to oxidation without catalysis by the enzyme. Upon administration it was not known if the compounds would act as strict vitamin K analogues or as competitive inhibitors of the GGCX (i.e these compounds could act as fully functional replacements for dihydrovitamin K, which would make them warfarin antagonists and coagulation-promoting agents, or competitive inhibitors of dihydrovitamin K which do not lead to carboxylation of the glutamate side chains, which would make them anticoagulants). However, it was anticipated that the action of GGCX on both of these compounds would convert them into structural analogues of vitamin K epoxide (UWEC-KO1, UWEC KO-2).

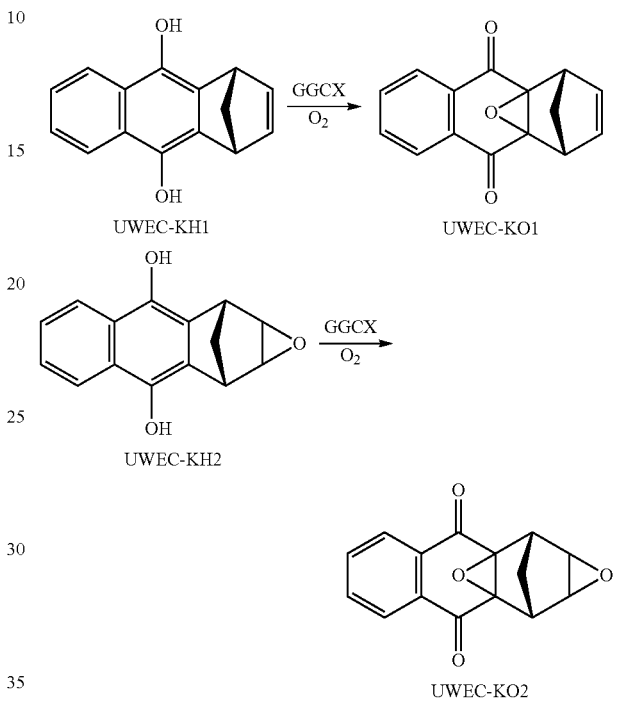

It was further anticipated that these compounds would function as inhibitors of the vitamin K epoxide reductase (VKOR), and most especially of the C-1 polymorph, which is important in warfarin inhibition of coagulation.

EXPERIMENTAL

Feeding Protocol.

Male, albino, Sprague-Dawley rats (n=100) weighing 150-175 g were placed in quarantine for 1 week and then housed in individual cages. To determine food consumption, rat chow in containers was weighed at the beginning and end of the day to determine the weight of the food consumed by each animal. The containers were modified to prevent spillage. Rats were provided with water ad libitum. The chow was composed of rolled oats, sugar and peanut oil (92:4:4) (w:w:w) plus a standard vitamin/mineral mix.

Administration of anticoagulant was accomplished by uniformly dispersing the compound in the peanut oil used in the chow. The anticoagulants were prepared to one of 3 concentrations: the $LD_{50}$ concentration for warfarin for a rat weighing 180 g (assuming a 30 g weight gain during quarantine), or 1 log concentration above or below the $LD_{50}$ concentration. The $LD_{50}$ for warfarin is 1 mg/kg/day for 5 days. Thus diets were constructed at 0.1 mpk/d. 1 mpk/d and 10 mpk/d. Actual concentration of the drug to be applied will be based on the average food consumption determined for the rats.

Groups of rats were established as follows for each UWEC-K compound:
 A. Diet (Negative) controls: no anticoagulant additive to food
 B. Positive controls: food treated with warfarin at $LD_{50}$ concentration for a rat weighing 180 g
 C. Control to evaluate potentiation or diminution of warfarin effect. (B plus D2)
 D. Experimental: food treated with UWECK compound at one of three doses
  1) equivalent dose of warfarin (0.25 mg/kg)
  2) 1 log concentration above the dose
  3) 1 log concentration below the $LD_{50}$ dose There were 10 animals each for groups A, B, C, D1, D2, and D3. The groups will be repeated for each of the two compounds. Four animals in each group were anaesthetized at 96 hours, and exsanguinated by cardiac puncture. Prior to exsanguination each animal was anesthetized by the intraperitoneal injection of 50 mg/kg of sodium pentothal. Blood was collected in 3.2% citrate in pediatric tubes and tested for prothrombin time and active coagulation factors VII and X. Factor V will also be tested as a marker of potential hepatic toxicity. The remainder of the animals were continued on their treatment protocol for a total time of 10 days, sacrificed as described above, and prothrombin time, levels of active coagulation factors V, VII and X, LDH, AST, ALT, Alkaline Phosphatase and creatinine were determined in plasma and serum extracted from the animals. Animals were monitored twice daily and any animals found in apparent distress with be immediately sacrificed as above.

The rationale for dose selection was as follows:
 Studies have shown that 0.25 mg/kg will maintain an INR of 2.6 in rats of approximately 200 gm BW
 The log dose both above and below this dose will give some understanding of a dose response curve for anticoagulant effect and look at potential toxic effects of the compound at large and small doses.

The outcome observations that were determined:
 Change in prothrombin time in animals treated with anticoagulants compared to controls
 Change in levels of factor VII and X in animals treated with anticoagulants compared to controls
 Change in level of factor V, LDH, AST, ALT, Alkaline Phosphatase and creatinine in any group (toxicity control)

The results of the feeding studies are gathered in Table 1 (4-day) and Table 2 (10-day).

TABLE 1

4-Day feeding results.

|  | Control | | Warfarin 0.25 mpk | | UWEC-K1 0.25 mpk | | UWEC-K2 0.25 mpk | |
| --- | --- | --- | --- | --- | --- | --- | --- | --- |
|  | Mean | SEM | Mean | SEM | Mean | SEM | Mean | SEM |
| Alk Phos | 244.55 | 15.92 | 242.30 | 19.16 | 245.75 | 26.81 | 240.33 | 27.94 |
| ALT | 52.18 | 6.67 | 46.00 | 3.78 | 41.75 | 1.31 | 45.00 | 4.00 |
| AST | 148.36 | 10.11 | 123.25 | 6.30 | 152.75 | 20.28 | 135.33 | 14.50 |
| LDH | 1603.64 | 170.33 | 1168.88 | 223.80 | 1168.00 | 244.21 | 1496.33 | 459.43 |
| Creat. | 0.11 | 0.01 | 0.11 | 0.01 | 0.10 | 0.00 | 0.10 | 0.00 |
| Pro Time | 12.76 | 0.48 | 36.98 | 5.89 | 11.60 | 0.06 | 11.63 | 0.09 |
| VII % | 400.00 | 33.16 | 29.54 | 4.12 | 351.33 | 11.22 | 334.33 | 26.30 |
| X % | 60.55 | 2.96 | 10.00 | 0.00 | 65.33 | 2.60 | 61.00 | 5.57 |

|  | UWEC-K1 2.5 mpk | | UWEC-K2 2.5 mpk | | UWEC-K1 0.025 mpk | | UWEC-K2 0.025 mpk | |
| --- | --- | --- | --- | --- | --- | --- | --- | --- |
|  | Mean | SEM | Mean | SEM | Mean | SEM | Mean | SEM |
| Alk Phos | 230.67 | 34.81 | 217.25 | 13.54 | 170.67 | 12.33 | 213.50 | 11.27 |
| ALT | 39.00 | 4.16 | 35.50 | 3.52 | 37.67 | 5.21 | 40.25 | 2.39 |
| AST | 125.67 | 22.39 | 114.75 | 7.60 | 121.00 | 13.08 | 104.75 | 8.34 |
| LDH | 1304.67 | 426.98 | 1026.50 | 140.70 | 1075.33 | 273.97 | 758.75 | 191.75 |
| Creat. | 0.10 | 0.00 | 0.10 | 0.00 | 0.15 | 0.03 | 0.10 | 0.00 |
| Pro Time | 11.78 | 0.31 | 12.73 | 0.65 | 11.18 | 0.21 | 11.38 | 0.17 |
| VII % | 370.75 | 7.35 | 395.50 | 18.00 | 346.75 | 33.59 | 366.25 | 7.75 |
| X % | 64.25 | 2.39 | 61.00 | 3.67 | 74.50 | 7.96 | 73.25 | 4.03 |

|  | UWEC-K1 2.5 mpk Warfarin 0.25 mpk | | UWEC-K2 2.5 mpk Warfarin 0.25 mpk | |
| --- | --- | --- | --- | --- |
|  | Mean | SEM | Mean | SEM |
| Alk Phos | 236.50 | 5.61 | 260.75 | 18.32 |
| ALT | 50.25 | 5.62 | 41.00 | 2.80 |
| AST | 93.50 | 5.98 | 105.75 | 9.72 |
| LDH | 183.25 | 26.25 | 583.75 | 209.73 |
| Creat. | 0.13 | 0.03 | 0.10 | 0.00 |
| Pro Time | 40.53 | 5.98 | 11.95 | 0.22 |
| VII % | 20.25 | 3.57 | 264.00 | 27.51 |
| X % | 4.75 | 1.49 | 58.75 | 3.35 |

TABLE 2

10-Day feeding results.

| | Control | | Warfarin 0.25 mpk | | UWEC-K1 0.25 mpk | | UWEC-K2 0.25 mpk | |
|---|---|---|---|---|---|---|---|---|
| | Mean | SEM | Mean | SEM | Mean | SEM | Mean | SEM |
| Alk Phos | 218.82 | 10.27 | 249.73 | 12.51 | 283.50 | 13.01 | 274.17 | 15.30 |
| ALT | 43.53 | 1.88 | 48.09 | 1.47 | 48.33 | 1.91 | 47.50 | 2.66 |
| AST | 106.41 | 6.33 | 91.82 | 3.24 | 121.33 | 7.38 | 118.67 | 2.92 |
| LDH | 833.59 | 88.80 | 626.18 | 66.72 | 1330.33 | 212.47 | 1445.50 | 74.70 |
| Creat. | 0.17 | 0.01 | 0.15 | 0.02 | 0.15 | 0.02 | 0.12 | 0.02 |
| Pro Time | 12.91 | 0.65 | 24.38 | 3.59 | 11.72 | 0.08 | 11.55 | 0.09 |
| VII % | 321.31 | 14.71 | 56.18 | 5.61 | 304.67 | 15.39 | 295.17 | 8.69 |
| X % | 58.06 | 1.81 | 14.85 | 1.79 | 61.17 | 2.12 | 59.83 | 2.71 |

| | UWEC-K1 2.5 mpk | | UWEC-K2 2.5 mpk | | UWEC-K1 0.025 mpk | | UWEC-K2 0.025 mpk | |
|---|---|---|---|---|---|---|---|---|
| | Mean | SEM | Mean | SEM | Mean | SEM | Mean | SEM |
| Alk Phos | 264.00 | 17.32 | 264.17 | 10.36 | 252.17 | 14.39 | 241.67 | 19.80 |
| ALT | 49.33 | 2.75 | 48.50 | 2.96 | 49.33 | 3.75 | 48.17 | 3.46 |
| AST | 124.67 | 8.78 | 110.67 | 6.18 | 134.67 | 6.96 | 132.33 | 13.73 |
| LDH | 1663.83 | 198.70 | 1234.50 | 167.47 | 1697.17 | 126.07 | 1552.33 | 244.01 |
| Creat. | 0.15 | 0.02 | 0.15 | 0.02 | 0.13 | 0.02 | 0.10 | 0.00 |
| Pro Time | 11.63 | 0.08 | 11.57 | 0.10 | 11.37 | 0.06 | 11.58 | 0.06 |
| VII % | 286.83 | 10.00 | 325.33 | 18.56 | 364.00 | 21.04 | 350.17 | 11.34 |
| X % | 61.00 | 1.81 | 63.33 | 1.38 | 68.00 | 0.63 | 64.17 | 1.49 |

| | UWEC-K1 2.5 mpk Warfarin 0.25 mpk | | UWEC-K2 2.5 mpk Warfarin 0.25 mpk | |
|---|---|---|---|---|
| | Mean | SEM | Mean | SEM |
| Alk Phos | 215.50 | 9.23 | 190.60 | 36.90 |
| ALT | 46.67 | 2.14 | 39.40 | 6.55 |
| AST | 101.33 | 7.61 | 101.00 | 12.51 |
| LDH | 653.33 | 198.97 | 795.20 | 281.92 |
| Creat. | 0.13 | 0.03 | 0.18 | 0.05 |
| Pro Time | 35.38 | 4.29 | 108.42 | 38.46 |
| VII % | 35.00 | 5.00 | 18.40 | 8.57 |
| X % | 7.67 | 1.15 | 3.60 | 1.21 |

The data in the tables relative to blood clotting are the Pro Time (the time required for prothrombin coagulation), VII % (a measure of the amount of clotting factor VII in the blood), and X % (a measure of the amount of clotting factor X in the blood. These data are combined rearranged with particular emphasis on these data into Table 3 (4 days) and Table 4 (10 days).

TABLE 3

Prothrombin coagulation time; Factor VII and Factor X at 4 days.

| Experiment | Pro Time | SEM | VII % | SEM | X % | SEM |
|---|---|---|---|---|---|---|
| Control | 12.76 | 0.48 | 400.00 | 33.16 | 60.55 | 2.96 |
| UWEC-K1 0.025 | 11.18 | 0.21 | 346.75 | 33.59 | 74.50 | 7.96 |
| UWEC-K1 0.25 | 11.60 | 0.06 | 351.33 | 11.22 | 65.33 | 2.60 |
| UWEC-K1 2.5 | 11.78 | 0.31 | 370.75 | 7.35 | 64.25 | 2.39 |
| UWEC-K2 0.025 | 11.38 | 0.17 | 366.25 | 7.75 | 73.25 | 4.03 |
| UWEC-K2 0.25 | 11.63 | 0.09 | 334.33 | 26.30 | 61.00 | 5.57 |
| UWEC-K2 2.5 | 12.73 | 0.65 | 395.50 | 18.00 | 61.00 | 3.67 |
| warfarin 0.25 | 36.98 | 5.89 | 29.54 | 4.12 | 10.00 | 0.00 |
| warfarin 0.25 + UWEC-K1 2.5 | 40.53 | 5.98 | 20.25 | 3.57 | 4.75 | 1.49 |
| warfarin 0.25 + UWEC-K2 2.5 | 11.95 | 0.22 | 264.00 | 27.51 | 58.75 | 3.35 |

TABLE 4

Prothrombin coagulation time; Factor VII and Factor X at 10 days.

| Experiment | Pro Time | SEM | VII % | SEM | X % | SEM |
|---|---|---|---|---|---|---|
| Control | 12.91 | 0.65 | 321.31 | 14.71 | 58.06 | 1.81 |
| UWEC-K1 0.025 | 11.37 | 0.06 | 364.00 | 21.04 | 68.00 | 0.63 |
| UWEC-K1 0.25 | 11.72 | 0.08 | 304.67 | 15.39 | 61.17 | 2.12 |
| UWEC-K1 2.5 | 11.63 | 0.08 | 286.83 | 10.00 | 61.00 | 1.81 |
| UWEC-K2 0.025 | 11.58 | 0.06 | 350.17 | 11.34 | 64.17 | 1.49 |
| UWEC-K2 0.25 | 11.55 | 0.09 | 295.17 | 8.69 | 59.83 | 2.71 |
| UWEC-K2 2.5 | 11.63 | 0.08 | 286.83 | 10.00 | 61.00 | 1.81 |
| warfarin 0.25 | 24.38 | 3.59 | 56.18 | 5.61 | 14.85 | 1.79 |
| warfarin 0.25 + UWEC-K1 2.5 | 35.38 | 4.29 | 35.00 | 5.00 | 7.67 | 1.15 |
| warfarin 0.25 + UWEC-K2 2.5 | 108.42 | 38.46 | 18.40 | 8.57 | 3.60 | 1.21 |

The most striking result from these tables is the behavior of UWEC-K2 over the time period of the experiment. At 4 days, UWEC-K2 is clearly an anti-warfarin: with the exception of the Factor VII levels, the administration of UWEC-K2 and warfarin gives results that are not significantly different from control. At 10 days, on the other hand, UWEC-K2 enhances the effects of warfarin to a significant degree: the prothrombin clotting time is increased by almost an order of magnitude compared to control, and by a factor of over 4 relative to warfarin alone; the levels of Factor VII are reduced by a factor of close to 20 compared to control, and by a factor of 3 relative to warfarin alone; the levels of Factor X are reduced by a factor of close to 20 compared to control, and by a factor of 4 relative to warfarin alone. This implies that at 10 days, UWEC-K2 quadruples the anticoagulant activity of warfarin.

These results can be viewed in the form of the plots in FIGS. 1-4. From these results, it is clear that at 4 days, the first six sets of results do not differ significantly from control, which is evidence that neither UWEC-K1 nor UWEC-K2 affects blood clotting time or the levels of the clotting factors VI and X. At 4 days administration, we find that UWEC-K2 is a strong inhibitor of the activity of warfarin, as shown in FIGS. 1 and 2. Note that the scale in FIG. 2 is logarithmic and illustrates how UWEC-K2 at 4 days effectively reverses the effects of warfarin: the clotting time falls, and the levels of both Factor VII and Factor X increase, although the level of Factor VII does not quite return to the level of control.

Just as at 4 days, the first six sets of results at 10 days do not differ significantly from control, which is evidence that neither UWEC-K1 nor UWEC-K2 affects blood clotting time or the levels of the clotting factors VII and X at this time. These FIGS. 1-4 do, however, show how both UWEC-K1, and much more effectively UWEC-K2 at 10 days both significantly enhance the effect of warfarin. In particular, after 4 days of the co-administration of warfarin and UWEC-K2, the blood analyses show that the UWEC-K2 leads to a substantial restoration of clotting factors VII and X, and a reduction in the prothrombin time to near control levels, despite the co-administration of warfarin, as is clearly evident from FIGS. 1-2. After 10 days of co-administration, the effects of the UWEC-K2 dramatically change, as is obvious from FIGS. 3-4. At this point in time, the activity of UWEC-K2 is reversed and it becomes a strong potentiator of the anticoagulant activity of warfarin, enhancing its activity by a factor of approximately 4.

The interpretation of these results of the anticoagulant studies is in terms of the initial hydrolysis of the ester groups of UWEC-K1 and UWEC-K2 to give the analogues of dihydrovitamin K, UWEC-KH1 and UWEC-KH2. Neither of these compounds functions as an enhancer of the anticoagulant activity of warfarin at 4 days, which is consistent with these compounds having to undergo an essential transformation prior to their enhancement of warfarin activity being revealed.

It is suggested that this required transformation is in the form of conversion of these compounds to the corresponding UWEC-KO analogues of vitamin K epoxide. This would mean that that both these compounds are substrates for GGCX, with UWEC-KH2 being not only a substrate, but also a functional substrate of the carboxylase, which allows it to promote the carboxylation of the clotting factors, and hence function as an inhibitor of the activity of warfarin. Clearly, UWEC-KH1 does not promote carboxylation of the clotting factors when it is oxidized by GGCX. Equally clearly, both UWEC-KH compounds are converted between 4 and 10 days into compounds (we suggest that these are UWEC-KO1 and UWEC-KO2) that, while not effective alone as oral anticoagulants, do act in concert with warfarin. This may indicate that both molecules (warfarin and the UWEC-KO compounds) bind to sites on VKORC-1 to prevent the reduction of vitamin K epoxide, and that this synergism is responsible for the enhanced activity of the warfarin.

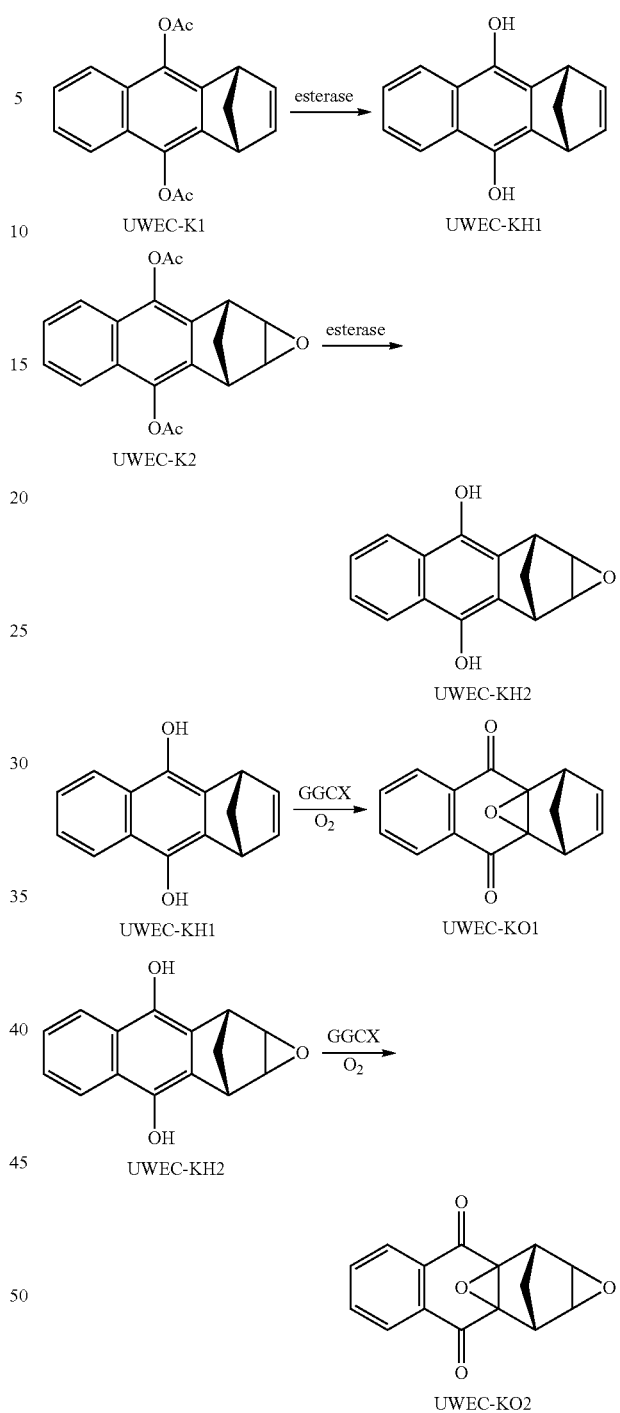

The difference between the two compounds is the presence, in UWEC-KO2, of a reactive epoxide ring that is absent from UWEC-KO1. This strongly suggests that this epoxide is important in the observed dramatic enhancement of the anticoagulant activity of warfarin. It is hypothesized that this marked synergism between warfarin and UWEC-KO2 may reflect a covalent linkage being formed between then while both are held in the binding sites on VKORC-1, as shown below.

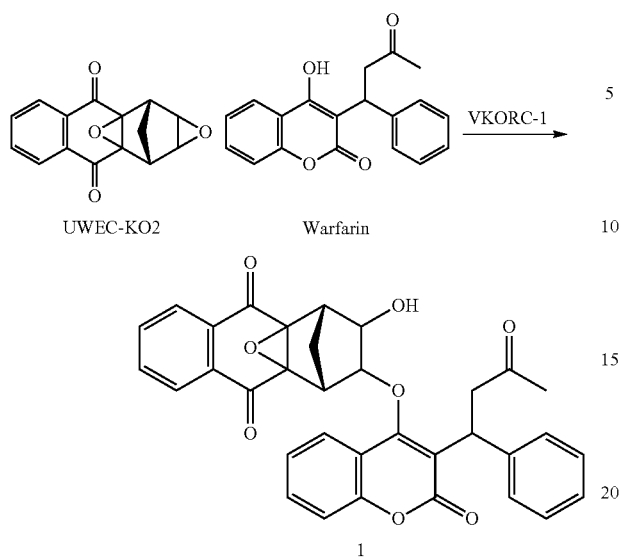

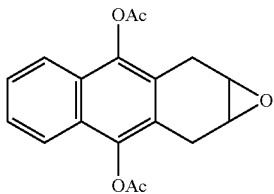
UWEC-K3

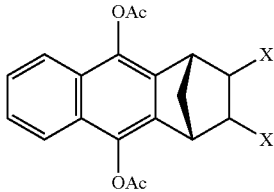
UWEC-K4

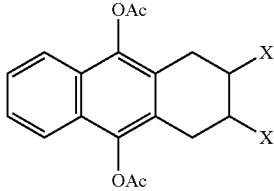
UWEC-K5

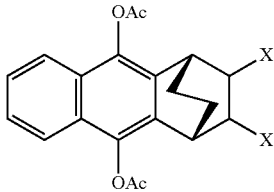
UWEC-K6

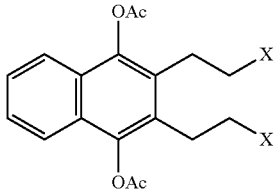
UWEC-K7

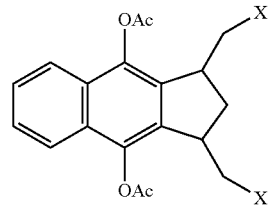
UWEC-K8

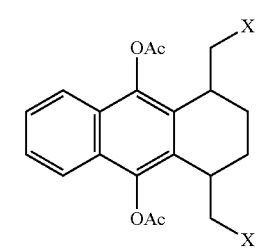
UWEC-K9

Implicit in this argument is the deduction that there are two warfarin binding sites in VKORC-1, and that UWEC-KO2 may bind to one of these sites, while warfarin binds to the second. This, in turn, raises the question of whether warfarin itself actually binds twice to VKORC-1 (this would provide one possible explanation of the lack of sensitivity of some populations to warfarin: if one or other of these two binding sites is mutated such that warfarin no longer fits the site, its anticoagulant activity would be reduced, if not eliminated).

If the two molecules are held in sufficiently close proximity to react, it is not unreasonable to hypothesize that molecules similar to UWEC-KO2 (or the pro-drug, UEWC-K2) should also function the same way. Thus, 2,3-disubstituted-1,4-naphthalenediol derivatives carrying a leaving group in the side chains might be expected to exhibit the same synergistic effect with warfarin. It is proposed that the compounds illustrated below all represent readily accessible analogues of the UWEC-K2 molecule. Eight general classes of these compounds are shown below. All have the same naphthalene ring system with the hydrolysable ester groups, and the same geometric relationship between the leaving group (an epoxide or halide or sulfonate ester) and the ring system. It is reasonable to expect that if UWEC-KH2 is a substrate for GGCX, these compounds, also, should be substrates for GGCX, so that all should be convertible to the UWEC-KO analogues. In these structures, X represents a group capable of reacting with the nucleophilic site on warfarin (presumably the 4-hydroxyl group), and is chosen from the group of the halogens, sulfonate esters, epoxides, and aziridines, acylaziridines, or sulfonylazirodines.

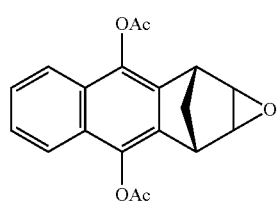
UWEC-K2

Various alternative embodiments are contemplated as being within the scope of following claims particularly pointing out and distinctly claiming the subject matter regarded as the present invention.

What is claimed is:

1. A compound comprising a structure according to formula I or formula II:

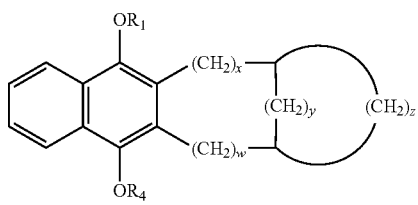

I

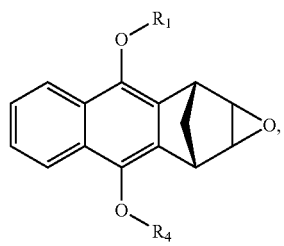

II

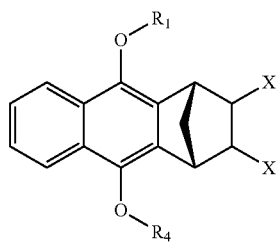

wherein $R_1$ and $R_4$ are hydrogen or acyl; and wherein X is selected from the group consisting of aziridine, N-acyl-aziridine, N-sulfonylaziridine, halide, and sulfonate ester.

2. The compound according to claim 1, wherein the compound has the structure:

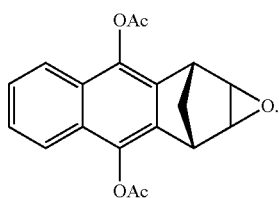 [SMILES: CC(=O)Oc1c2c(c(OC(C)=O)c3ccccc13)[C@@H]1C[C@H]2C2OC21]

3. A method of increasing the anticoagulant activity of warfarin, comprising administering to a subject an effective amount of warfarin and an anticoagulant compound according to claim 1.

* * * * *